United States Patent [19]
Gelley

[11] Patent Number: 4,899,734
[45] Date of Patent: Feb. 13, 1990

[54] SPECULUM WITH ARRESTING DEVICE

[75] Inventor: Doris Gelley, Gateshead, Great Britain

[73] Assignee: Ottes Trading S.A., Panama City, Panama

[21] Appl. No.: 166,068

[22] Filed: Mar. 9, 1988

[30] Foreign Application Priority Data

Mar. 10, 1987 [CH] Switzerland ............................ 885/87

[51] Int. Cl.⁴ ............................ A61B 1/32; B25B 7/14
[52] U.S. Cl. .......................................... 128/17; 81/318; 81/385; 606/205; 606/198
[58] Field of Search ................ 81/318, 319, 320, 324, 81/325, 385, 393, 427.5, 345; 128/17, 18, 19, 321, 322, 323, 324; 439/468

[56] References Cited

U.S. PATENT DOCUMENTS

| | | | |
|---|---|---|---|
| 1,190,031 | 4/1916 | Spalding | 81/319 |
| 3,528,409 | 9/1970 | Bruder | 128/17 |
| 3,926,195 | 12/1975 | Bleter et al. | 128/321 |
| 4,127,315 | 11/1978 | McKee | 439/468 |
| 4,282,783 | 8/1981 | Fortune | 81/427.5 |

FOREIGN PATENT DOCUMENTS 836545  4/1952 Fed. Rep. of Germany ...... 128/321
2802403 4/1979 Fed. Rep. of Germany ...... 128/321

Primary Examiner—Richard C. Pinkham
Assistant Examiner—Mark Graham

[57] ABSTRACT

An arresting member (5) is rotatably mounted about the lengthwise axis of a lever handle (2) of a pair of pliers. The arresting member (5) is directed towards the other lever handle (1) and penetrates with its free end (11) through a slot (12) in this other lever handle (1). The shank (13) of the arresting member (5) is flattened so that the arresting member in one rotational position can axially freely slide in the slot (12). The largest radial extent of the shank (13) slightly exceeds the width of the slot (12) so that the arresting member (5) is clamped in another rotational position in the slot (12). By fabricating the arresting member (5) from a deformable material, the pair of pliers can be operated also with the arresting pin in this rotational position. Upon sliding through the slot (12) the arresting member (5) is thereby deformed. By the static friction existing in the rest position between the arresting member (5) and the edges (15) of the slot, the pair of pliers are however locked in each spreading position into which it is brought. In this manner, it is possible to operate with one hand the pair of pliers including the arresting device.

5 Claims, 1 Drawing Sheet

SPECULUM WITH ARRESTING DEVICE

BACKGROUND OF THE INVENTION

The invention relates to a pair of pliers with an arresting device for the arresting thereof in a clamping position.

The term pliers is hereby to be understood in the broadest sense and should thus not only include so-called clamping pliers in which, upon movement of the lever handles towards each other, the jaws of the pliers move toward each other and clamp an object therebetween, but also so-called spreading pliers in which the movement of the lever handles towards each other is transformed into a spreading apart of the jaws of the pliers. Typical pliers of the last-mentioned type are, by way of example, the speculae used for medical purposes, and which serve for widening body openings for examinations and operations.

In both cases the arresting device serves for arresting the pair of pliers in the momentary spreading position, which corresponds with the desired or required clamping pressure of the jaws inwardly or outwardly.

A speculum for gynaecological examinations is known, in which the arresting member is formed by a pin with a flat, for example, oval or rectangular cross-section, which at the narrow edges thereof is provided with thread-type ribs. This pin is rotatably fastened about its lengthwise axis at the one lever handle of the speculum and projects perpendicularly away from this one lever handle toward the other lever handle. The pin penetrates with its free end through an elongate slot in said other lever handle. The opening width of this slot is larger than the pin body, yet smaller than the extent of the pin including the ribs thereof. If therefore the pin is in a rotational position in which the ribs of the pin are directed against the ends of said slot, the lever handles can be freely moved towards each other or spread apart from one another, whereby the pin slides in the slot in accordance with the momentary spreading position of the lever handles and that concerns not only the extent of penetration but also the position of the pin within the lengthwise extent of the slot. When the desired clamping position is reached, this position can be arrested by turning the pin through 90° in that namely the lengthwise edges of the slot are caught in each case between two adjacent ribs of the pin on the opposite narrow sides thereof and every further forward or backward sliding of the pin in the slot is prevented. To release this arresting action, it is then sufficient to rotate the arresting pin about the lengthwise axis thereof until the ribs withdraw from the region of the edges of the slot, whereby the arresting action is eliminated and the arresting pin can freely slide in the slot. Consequently, the lever handles can be moved without hindrance.

The advantage of this previously known pair of pliers, is namely that it can be frequently used because the arresting action wears out only slowly, but on the other hand these pliers are associated with the disadvantage that the user needs both hands for the arresting action, namely one hand to clamp the pair of pliers by means of the lever handles and to hold the pair of pliers in the desired clamping position and the other hand to rotate the arresting pin in the last-mentioned clamping position and to lock the clamping position.

In pliers of the known type for medical usage, the aforementioned advantage is attained at the expense that the pair of pliers is fabricated from a sterilizable material. Nowadays however, the trend is, as is already the case with syringes, towards instruments which are provided only for one-time usage, so that the mentioned advantage has appreciably lost significance at least as concerns pliers for medical usage.

SUMMARY OF THE INVENTION

The invention solves the problem of providing a pair of pliers which can be operated with one hand.

The problem is solved by a pair of pliers which have an arresting member wherein at least the surface of the arresting member is composed of a deformable material, which is deformable upon clamping the pliers with the arresting member in the arresting position.

By these measures, each spreading position of the lever handles achieved upon clamping the pair of pliers, which is done with one hand in the usual way, is automatically fixed without requiring any special manipulation of arresting means with the other hand. The clamping of the pair of pliers also can be effected in steps up to the desired clamping position.

The arresting member can be provided only at its surface with a coating of a deformable material, however it is expedient to fabricate the entire arresting member from such a deformable material, for example, from an elastic plastic material, whereby at least the lever handle with the aforementioned opening is composed of a harder plastic material and the edges of the opening in said other lever handle, which edges cause the arresting deformation of the arresting member, advantageously possess a sharp engaging edge, which augments the deformation of the arresting member and the clamping thereof in this lever handle. When thereby, in addition, these edges are oppositely directed to the movement of the lever handle for clamping the pair of pliers, then, on the one hand, the sliding of the arresting member in the opening is facilitated upon clamping the pliers, while conversely a sliding back is effectively prevented under the effect of the counteracting force, because the edges thereby immediately claw more intensively into the soft material of the arresting member.

DESCRIPTION OF THE PREFERRED EMBODIMENT

Figure 1:
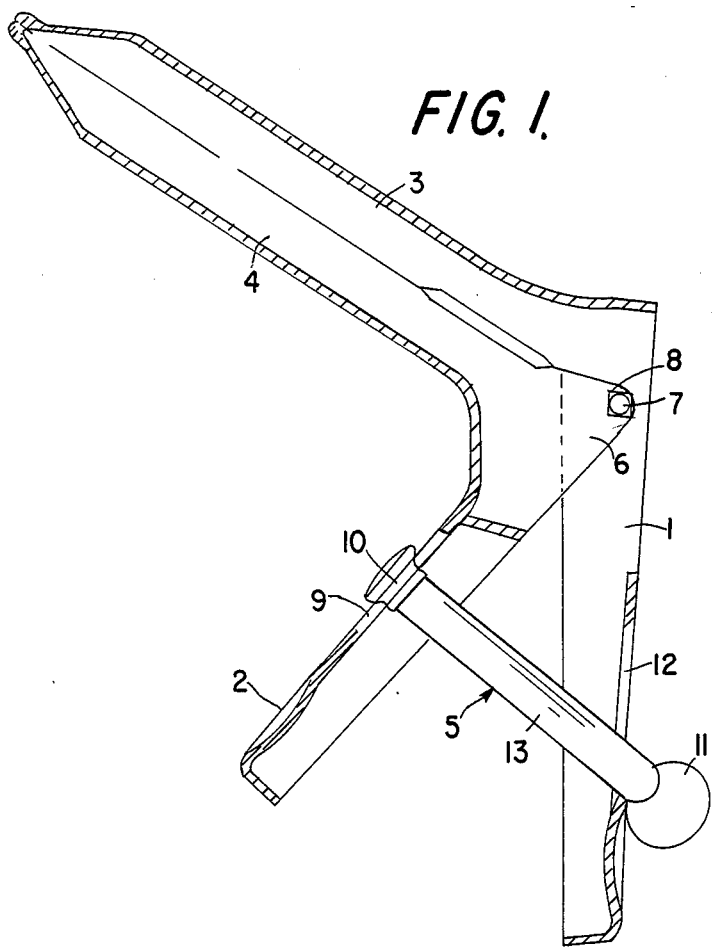
FIG. 1 shows a section through a speculum in the closed condition.

The illustrated speculum consists in total of three plastic parts, namely both of the lever handles 1 and 2 with the clamping jaws 3 and 4, respectively, and an arresting member 5. The clamping jaw 3 is formed in an obtuse angle and the clamping jaw 4 in an acute angle at the associated lever handle 1 and 2, respectively. Hinge tabs 6 at the transition from the lever handle 2 to the clamping jaw 4 extend into a recess in the transition from the lever handle 1 to the clamping jaw 3. They carry pins 7 at their outer side which can be each inserted into an aperture 8 of the part 1, 3 to form the plier hinge. In the closed condition of the speculum illustrated in FIG. 1, both the clamping jaws 3 and 4 form a cylindrical body which is conically converging at the front end and is suitable to be introduced into a body cavity to be examined or treated and both of the lever handles 1 and 2 are spread apart.

Figure 2:
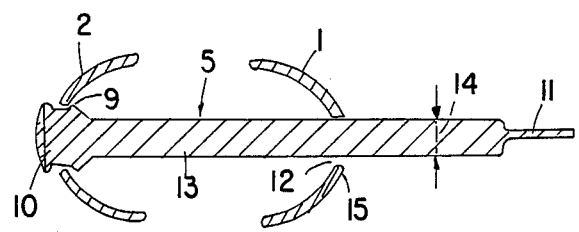
FIG. 2 shows a section through the two lever handles of the speculum and through the arresting member in the rotational position in accordance with FIG. 1.
Figure 3:
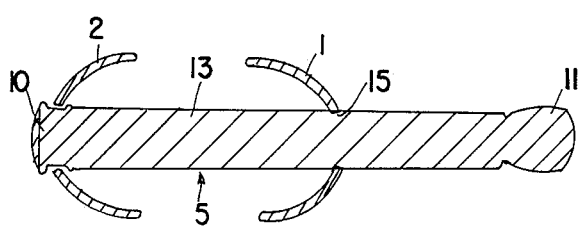
FIG. 3 shows a section corresponding with that of FIG. 2 but with the arresting member turned into the arresting position.

Both of the lever handles 1 and 2 are penetrated by the arresting member 5, whereby a short slot 9 in the lever handle 2 receives rotatably but axially non-displaceably the one end 10 of the arresting member 5. The arresting member 5 penetrates with its other free end through a slot 12 in the other lever handle 1. The end of the arresting member 5 projecting out of this slot 12 comprises a disc-shaped flattening 11 which facilitates the turning of the arresting member 5 with two fingers. As can be seen in FIGS. 2 and 3, the shank 13 of the arresting member 5 has the form of a flattened pin with an oval, elliptical or rectangular cross-section.

As already mentioned at the outset, a speculum of the type as heretofore described is known. The thickness 14 of the arresting pin of this known construction is smaller than the opening width of the slot 12. In the position of rotation shown in FIGS. 1 and 2, the arresting member 5 slides freely axially in the slot 12 when the spreading position of both the lever handles 1, 2 is changed for opening or closing the speculum. In usage, the mutually abutting clamping jaws 3, 4 according to FIG. 1 are introduced into the body cavity to be examined or treated and subsequently spread apart by moving the two lever handles 1 and 2 against one another about the hinge 7, 8 as a pivot. To arrest the desired open position, the arresting member in the case of the known speculum must be then turned through approximately 90° in order that the ribs protruding from the narrow side thereof, as explained at the outset, are caused to engage with the edges of the slot 12. While the operator turns the arresting pin with one hand into the arresting position, the operator must hold with the other hand both lever handles in the desired position.

Here the present invention intervenes in order to simplify this cumbersome operation, particularly, to render it possible to operate single-handedly. For this purpose, the arresting member 5 of the pair of pliers according to the invention is fabricated from a soft, deformable material, e.g. from an elastic plastic material such as the material known under the trademark MOPLEN, or is provided at least at its surface with a layer of such material, while the lever handles 1, 2 together with the clamping jaws 3, 4 are fabricated from a hard or in any case harder material than the material of the arresting member. Furthermore, as depicted in FIGS. 2 and 3, the edges of the slot 12 in the lever handle 1 are advantageously formed as a sharp cutting edge 15. The shank 13 of the arresting member 5 comprises in the plane of the flattening thereof an extent, which slightly exceeds the opening width of the slot 12, while the extent perpendicular thereto is smaller than the opening width of the slot 12.

Due to this construction, the sharp-edged edges 15 of the slot 12 are constantly pressed into the surface of the arresting member 5 when this arresting member is in the arresting rotational position which is shown in FIG. 3. By virtue of the soft material of which the arresting member 5 or at least the surface thereof consists, it is still possible to change the spreading of both the lever handles 1, 2. The edges 15 of the slot 12 then slide along the arresting member 5 under constant deformation thereof. As soon as the relative motion of the two lever handles 1, 2 is interrupted, the spreading achieved at this moment is, however, fixed by the static friction existing in the rest position. If then, in addition, as shown in the illustrated example, the sharp cutting edges 15 of the slot 12 are oppositely directed to the closing motion of the lever handle, the sliding of the arresting member 5 in the slot 12 is, on the one hand, facilitated upon clamping the pair of pliers, while conversely a sliding back under the action of the counterforce is effectively prevented by the thereby occurring increased clawing-in of the edges 15 into the material of the arresting member 5.

Unlike the known speculum hereinbefore described, the arresting member 5 in the pair of pliers according to the invention is turned before use thereof into the arresting position shown in FIG. 3. The actuation is effected as usual by moving with one hand the lever handles 1 and 2 towards one another. However, in contrast to the known construction, each attained spreading position of the lever handles 1, 2 is thereby automatically arrested. The pair of pliers can be operated with one hand and also in steps, whereby the latter is particularly advantageous in a construction such as a speculum, because during the examination of treatment, for which one hand possibly operates an instrument inserted into the body cavity expanded by the speculum and the other hand holds the pair of pliers which is actuatable for the purpose of achieving a larger enlargement of the body cavity, whereby then the new setting is again automatically fixed.

After terminating the treatment or examination, the arresting member is turned, as heretofore known, into the rotational position shown in FIG. 2, whereby the arresting action is released and the pair of pliers return or can be moved back without resistance into the starting position thereof.

It is obvious that the described arresting action is not only applicable for spreading pliers, particularly in a speculum, but just as well and with analogous advantages also in clamping pliers.

I claim:

1. A pair of pliers comprising a pair of lever handles with an arresting device means for arresting said pliers in a clamping position, said pliers having an elongated arresting member rotatably secured at one lever handle for rotation about its lengthwise axis, directed towards the other lever handle and extending with its free end through an opening in this other lever handle, which arresting member in one rotational position is axially freely slidable in this opening and by rotation into an arresting position is clampable with the edges of said opening in order to fix an attained spreading position of both lever handles, wherein at least the surface of the arresting member (5) is composed of a deformable material, which is deformable upon clamping the pliers with the arresting member in the arresting position and upon sliding through the edges (15) of the opening (12) in said other lever handle (1) and which, by means of the static friction existing in the rest position, arrest the lever handles (1, 2) in each spreading position in which the lever handles are brought.

2. The pair of pliers according to claim 1, the entire arresting member (5) is composed of a deformable material, said deformable material being an elastic plastic material and at least the lever handle (1) with said opening (12) is composed of a harder plastic material.

3. The pair of pliers according to claim 1 or 2, characterized by the features that the edges of the slot-shaped opening (12) in said other lever handle (1) comprise a sharp cutting edge (15), which augments the deformation of the arresting member (5) and the clamping thereof in this lever handle (1).

4. The pair of pliers according to claim 3, characterized by the features that upon clamping the pair of pliers the edges (15) of the opening (12) are transverse to the direction of movement of the lever handle (1) containing this opening.

5. The pair of pliers according to one of claims 1, 2, or 4, characterized by the features that the shank (13) of the arresting member (5) is formed by a flattened pin with an oval, elliptical or rectangular cross-section, the extent of which pin in the major axis of the cross-section thereof somewhat exceeds the opening width of the slot (12) in said other lever handle (1), while the extent of its minor axis is smaller than the width of said slot (12).

* * * * *